United States Patent
Tamburrino et al.

(10) Patent No.: US 7,371,066 B2
(45) Date of Patent: May 13, 2008

(54) ILLUMINATED DENTAL EXAMINATION INSTRUMENT

(75) Inventors: Richard A. Tamburrino, Auburn, NY (US); Jack L. Connelly, Camillus, NY (US); Catherine R. Wojnowicz, Auburn, NY (US); Bruce H. Schwager, Rochester, NY (US); Dongmin Yang, Syracuse, NY (US); Raymond A. Lia, Auburn, NY (US); Jeffrey J. Perkins, Tully, NY (US); Roger W. Leseberg, Syracuse, NY (US); Michael T. McMahon, Syracuse, NY (US)

(73) Assignee: Miltex, Inc., York, PA (US)

( * ) Notice: Subject to any disclaimer, the term of this patent is extended or adjusted under 35 U.S.C. 154(b) by 91 days.

(21) Appl. No.: 10/941,530

(22) Filed: Sep. 15, 2004

(65) Prior Publication Data

US 2006/0057536 A1    Mar. 16, 2006

(51) Int. Cl.
*A61C 3/00* (2006.01)
(52) U.S. Cl. .................................. 433/30; 362/138
(58) Field of Classification Search ............. 433/29, 433/30–31; 362/109, 138, 800
See application file for complete search history.

(56) References Cited

U.S. PATENT DOCUMENTS

| | | | |
|---|---|---|---|
| 4,907,135 A * | 3/1990 | Tarrson et al. .............. 362/109 |
| 4,993,945 A | 2/1991 | Kimmelman et al. |
| 5,139,421 A * | 8/1992 | Verderber .................... 433/31 |
| 5,274,943 A * | 1/1994 | Ratcliffe et al. ............... 43/17 |
| 5,385,468 A | 1/1995 | Verderber |
| 5,415,543 A * | 5/1995 | Rozmajzl, Jr. ............... 433/29 |
| 5,457,611 A * | 10/1995 | Verderber .................... 362/572 |
| D370,063 S | 5/1996 | Spreckelmeier |
| 5,741,132 A | 4/1998 | Usui et al. |
| 6,247,924 B1 | 6/2001 | Gunnarsson |
| 6,318,996 B1 | 11/2001 | Melikechi et al. |
| 6,443,729 B1 | 9/2002 | Watson |
| 6,544,036 B1 | 4/2003 | Brattesani |
| 6,560,038 B1 | 5/2003 | Parkyn, Jr. et al. |
| 6,575,744 B1 | 6/2003 | Oshida |
| 6,702,577 B2 | 3/2004 | Wong |
| 2002/0197582 A1 | 12/2002 | Cao |
| 2003/0076281 A1 | 4/2003 | Morgan et al. |
| 2003/0081430 A1 * | 5/2003 | Becker ....................... 362/573 |
| 2003/0107652 A1 | 6/2003 | Williams |
| 2003/0133292 A1 | 7/2003 | Mueller et al. |
| 2003/0207229 A1 * | 11/2003 | Wong ........................... 433/31 |
| 2004/0023184 A1 | 2/2004 | de Josselin de Jong et al. |
| 2004/0029069 A1 * | 2/2004 | Gill et al. ...................... 433/29 |
| 2004/0141336 A1 * | 7/2004 | West et al. .................. 362/555 |
| 2004/0154906 A1 * | 8/2004 | Qiu ........................... 200/11 R |
| 2004/0229187 A1 | 11/2004 | Bretscher et al. |
| 2005/0196721 A1 * | 9/2005 | Jackson et al. ............... 433/29 |
| 2005/0282102 A1 * | 12/2005 | Kert ............................. 433/29 |

* cited by examiner

*Primary Examiner*—Ralph A. Lewis
(74) *Attorney, Agent, or Firm*—Jones Day (57) ABSTRACT

An intraoral dental instrument includes an elongate handle or body and a mirror that is releasably attachable to a distal end thereof. An LED housing disposed in the handle proximate a light entrance surface of the mirror includes a housing body sized to retain at least one LED and a reflector attached to a distal end of the housing body. The reflector has an inwardly tapered cavity covering a LED lens envelope for focusing illumination from the at least one LED onto a portion of the light entrance surface of the mirror.

22 Claims, 9 Drawing Sheets

"OFF" POSITION

FIG.9

"ON" POSITION

ILLUMINATED DENTAL EXAMINATION INSTRUMENT

FIELD OF THE INVENTION

This invention relates to the field of medical diagnostic instruments and more particularly to an improved design for mounting at least one LED in a medical diagnostic instrument so as to provide more effective illumination, for example, in an intraoral dental mirror.

BACKGROUND OF THE INVENTION

Intraoral dental mirrors are repletely known in the field of dentistry as convenient apparatus for aiding in the inspection of the teeth of a patient. Typically, these instruments include an elongated handle having a retroflexed mirrored portion that permits inspection of both the upper and lower arches of teeth. Illuminated versions of these devices typically include a halogen lamp or other similar miniature light source, such as described in U.S. Pat. Nos. 5,741,132 and 6,575,744B1, that is provided beneath the mirror in a retroflexed portion of the instrument, or as described in U.S. Pat. Nos. 5,139,421 and 5,457,611, to Verderber, in which a miniature halogen or other incandescent bulb that is retained within the handle of the instrument is optically coupled to a light guide having the mirror portion, the guide being releasably attached to the distal end of the instrument.

One problem encountered in the use of incadescent bulbs as an illumination source in instruments, such as those described above, relates to heat generation developing from the contained bulb, thereby requiring the placement of suitable heat sinks or other heat dissipation means in the instrument and/or the use of open slotted vents in the gripping handle thereof. These solutions to the above problem complicate the overall design and manufacture of the instrument, including the cost thereof.

It has been considered with evolving technological advances to possibly utilize light emitting diodes (LEDs) as a light source in lieu of miniature halogen bulbs. Overall, LEDs are less sensitive to shock damage than incandescent bulbs or lamps, have an increased overall life, generate less heat, are more efficient, and are available in a wider range of color temperatures. A problem in using these light sources, however, has been in achieving sufficient illumination output for purposes of examination.

SUMMARY OF THE INVENTION

It is therefore a primary object of the present invention to overcome the above-noted deficiencies of the prior art.

It is another primary object of the present invention to provide improved illumination/coupling to enable at least one LED to be effectively used, for example, in an intraoral dental examination instrument.

Therefore and according to a preferred aspect, there is provided a light reflector for coupling the illumination output of at least one LED mounted for use in an intraoral dental examination instrument, said light reflector including an inwardly tapered cavity that is adapted to cover the lens envelope of the at least one LED.

Preferably, the light reflector can be positioned and/or adapted in relation to the at least one LED to focus the rays emitted by the at least one LED onto a light transmissive light guide (e.g., a disposable mirror) that is placed in proximity thereto.

According to another preferred aspect of the present invention, there is provided an illumination housing for an intraoral dental examination instrument, said illumination housing comprising: a housing body; at least one LED disposed in a distal end of said housing body; and a reflector attached to the distal end of said housing body, said reflector having an inwardly tapered cavity sized to cover the LED lens envelope so as to focus light from said at least one LED onto an attached transmissive mirror.

According to yet another preferred aspect, there is disclosed an intraoral dental examination instrument comprising:

an elongated gripping handle;

a mirror releasably attachable to a distal end of said handle; and an illumination housing disposed in the distal end of said handle proximate a light entrance surface of said mirror, said housing including a housing body sized to retain at least one LED and a reflector attached to a distal end of said housing body, said reflector having an inwardly tapered cavity covering a LED lens envelope for focusing illumination from said at least one LED onto a portion of said light entrance surface of said mirror. The illumination housing also contains driver circuits for the at least one LED on a printed circuit board.

The dental examination instrument preferably includes a switch assembly that is provided at the rear or proximal end of the handle, the switch assembly according to one version preferably including a retractable plunger permitting the user to selectively provide electrical contact between a set of contained batteries and the electrical contacts of the illumination housing, so as to energize the at least one contained LED and transmit the emitted light therefrom to the attached mirror. According to another version, the switch assembly is defined by a rotatable portion of the handle that selectively permits the at least one LED to remain illuminated during use.

An advantage of the present invention is that the reflector of the LED housing is raised above the LED lens envelope so as to protect the at least one LED from impact and/or shock loads or other damage that can occur, for example, during shipping, handling of the instrument, and during disassembly when removing the batteries.

Yet another advantage provided by the reflector of the present invention is improved optical coupling between the at least one LED and the mirror, thereby increasing illumination output.

Yet another advantage provided by the present invention is that the present instrument is cordless, and is therefore quite convenient for the caregiver (e.g., dentist or hygienist) to utilize, the instrument preferably being conveniently powered by a set of rechargeable batteries.

Still another advantage of the present invention is that less heat is generated using at least one LED as an illumination source rather than an incandescent bulb while producing sufficient illumination for examination purposes.

Still another advantage of the present instrument is that it can be easily disassembled so that the batteries and illumination housing can be set aside, allowing the handle portions can be autoclaved (e.g., sterilized).

These and other objects, features and advantages of the present invention will become apparent from the following Detailed Description which should be read in conjunction with the accompanying drawings.

DETAILED DESCRIPTION

The following description relates to an intraoral dental examination instrument that is made in accordance with certain preferred embodiments of the present invention. Throughout the course of discussion that follows several terms, such as "top", "side", "lateral", "bottom", "distal", "proximal", "front", "rear", and the like are used in order to provide a convenient frame of reference with regard to the accompanying drawings. These descriptions, however, unless indicated otherwise, should not be regarded as limiting with regard to the present invention.

Figure 1A:
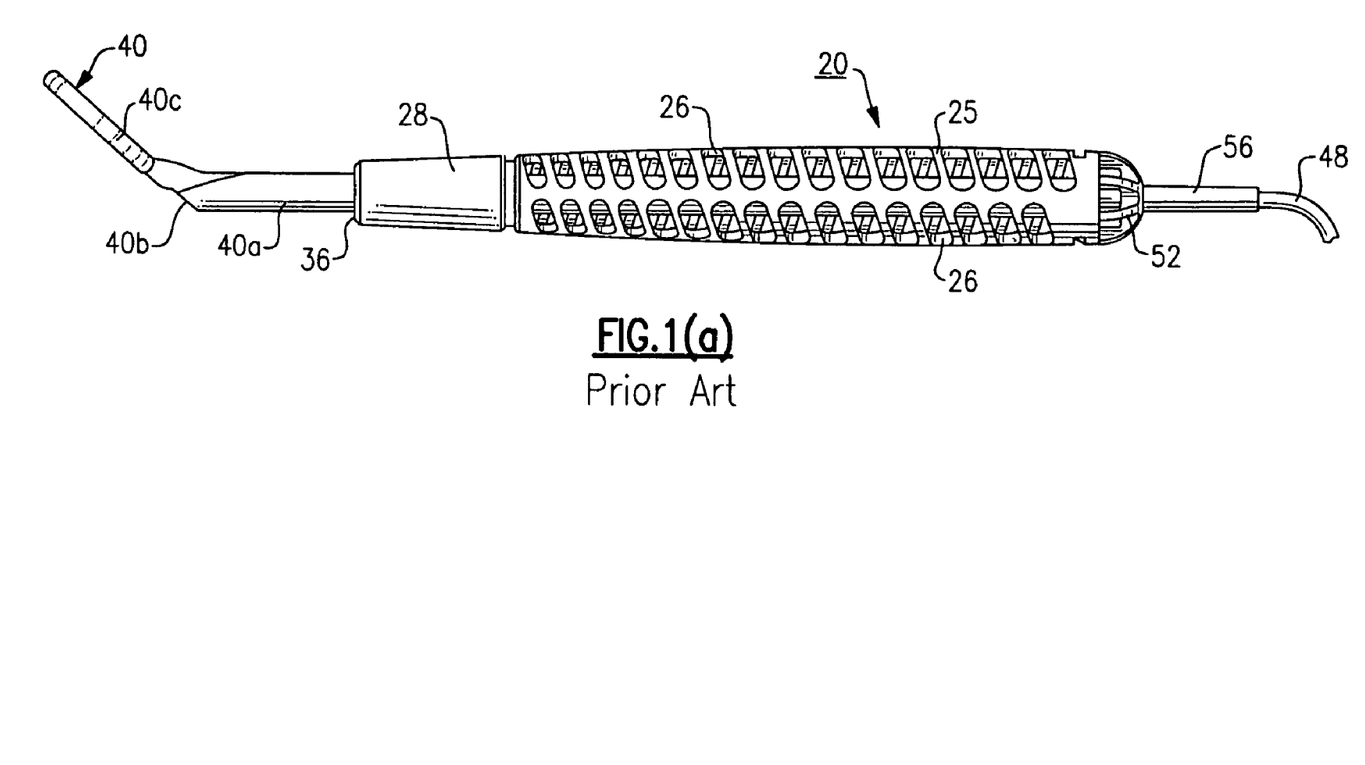
FIGS. 1(a) and 1(b) represents a side perspective view and a partially sectioned view, respectively, of a prior art intraoral dental examination instrument.
Figure 1B:
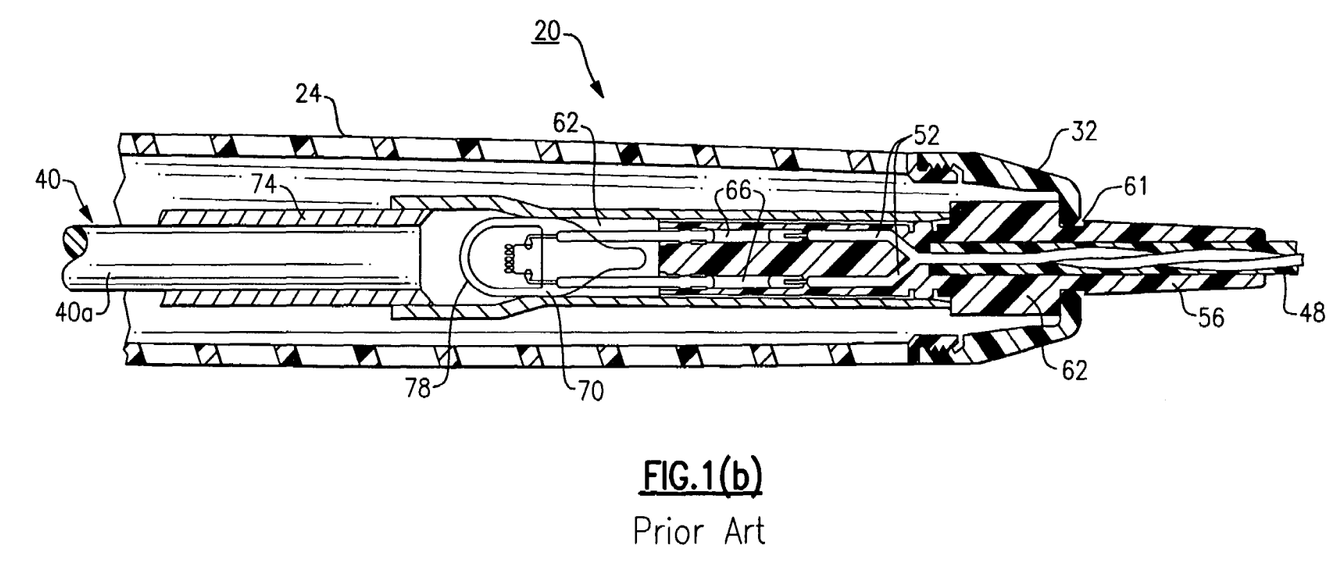

Prior to discussing the present invention and referring first to FIG. 1, there is illustrated an intraoral dental examination instrument 20 (partially shown according to the figure) that is made in accordance with the known art, described herein for background purposes. The examination instrument 20 is defined by an elongated body section 24, a front end cap 28 and a rear end cap 32, each preferably made from a moldable plastic or from any suitable low heat absorbing material.

Inserted into the front or distal end 36 of the front end cap 28 of the examination instrument 20 is a mirror 40 having a shank portion 40a, a heel portion 40b, and a face portion 40c. Mirror 40 is of the type that is described in greater detail in U.S. Pat. Nos. 5,457,611 and 5,139,421, in which light transmitted into the shank portion 40a from a contained bulb is emitted from the heel portion 40b and the face portion 40c on both facing sides of the mirror 40. The subject matter of each of the above-noted patents is herein incorporated by reference in its entirety. An electrical cord 48 containing a pair of wires 52 is inserted into the rear end cap 32, using a cord grip 56, to provide the energy from an exterior power supply (not shown) such as, for example, a 110 volt wall outlet, in order to operate the examination instrument 20.

The front end of the body section 24 of the instrument 20 includes a plurality of collet-like sections (not shown) as well as a threaded section (not shown) enabling interconnection of the front end cap 28 to the body section 24 as well as the mirror 40 to the instrument. When the mirror 40 is inserted into the front end of the body section 24, the front end cap 28 is rotated onto the end of the body 24 by virtue of mating threaded sections on each of the body and the front end cap, respectively, with the collet-like segments being caused to tighten around the shank portion 40a of the mirror 40, thereby holding the mirror securely in position within the elongated body section 24 of the instrument 20. Additional detail is provided in the above incorporated U.S. Pat. Nos. 5,457,611 and 5,139,421.

Referring to FIG. 1(b), the electrical cord 48 extending from an external power supply (not shown), is received within a molded lamp assembly unit 62 that is situated at the rear end of the body section 24 through an opening 61 formed in the rear end cap 32 and wires 52 are attached into the unit to a pair of electrical connectors 66. A miniature high intensity lamp 70, such as a miniature halogen bulb, is connected to the opposite ends of the connectors 66. The lamp 70 is positioned within the confines of the elongated body section 24 at one end of a heat sink 74 at close approximation to the shank portion 40a of the mirror 40, the latter being made from a light transmissive material, the lamp further containing a lens 78 that is configured and designed for focusing the light from the lamp into the end of the shank portion 40a. The heat sink 74 is extensive for purposes of this instrument 20 and includes separate portions that cover each of the lamp assembly unit 62 and light transmissive shank portion 40a of the mirror 40. In addition, a light weight gripping handle 25 covering the elongated body portion 24 includes a series of vent holes 26 also used for dissipating the heat that is generated by the instrument during use. As noted, additional details relating to this examination instrument 20 are described in U.S. Pat. No. 5,454,611, previously incorporated by reference herein.

Figures 2, 3:
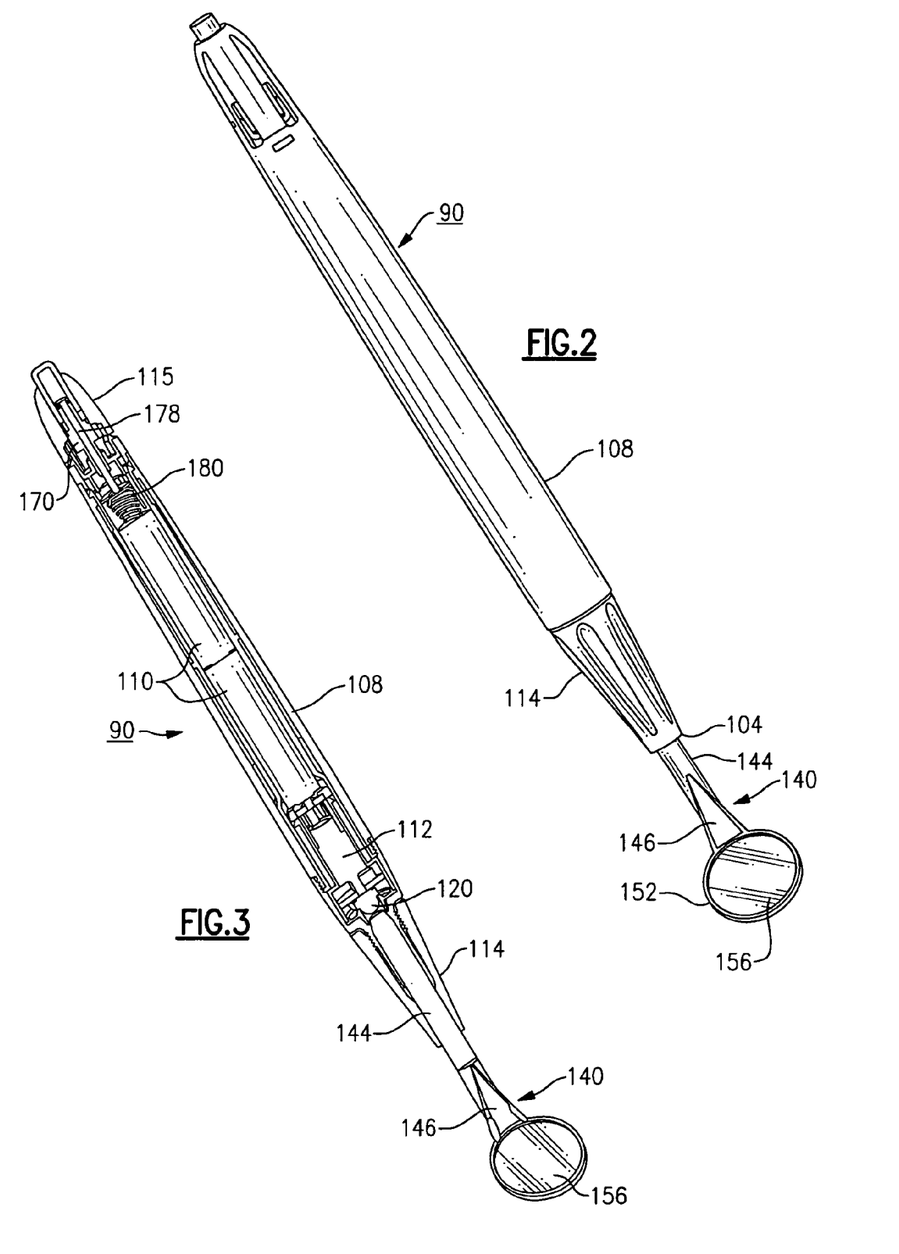
FIG. 2 is a top perspective view of an intraoral dental examination instrument made in accordance with a preferred embodiment of the present invention.
FIG. 3 is a sectioned view of the intraoral dental examination instrument of FIG. 2.

Referring now to FIGS. 2 and 3, there is shown an intraoral dental examination instrument that is made in accordance with a preferred embodiment of the present invention. The instrument 90, as now described in brief, includes an elongated body 108 that, like the preceding, includes a front end cap 114 and a rear end cap 115, respectively, each of which are releasably attached to the body as well as a mirror 100 that is preferably releasably attached to a distal end 104 of the instrument. The front end cap 114, include threaded portions that engage with respective threaded portions formed in the front end of the body 108. The rear cap 115 according to this embodiment snaps into place onto the rear or proximal end of the body 108. Preferably the body 108, as well as the front and rear end caps 114, 115, are each manufactured from plastic or a similar low heat absorbing material, such as Radel-R, polyphenylsulfone, or suitable polymer or other low heat absorbing material that permits autoclaving.

Figures 4, 5:
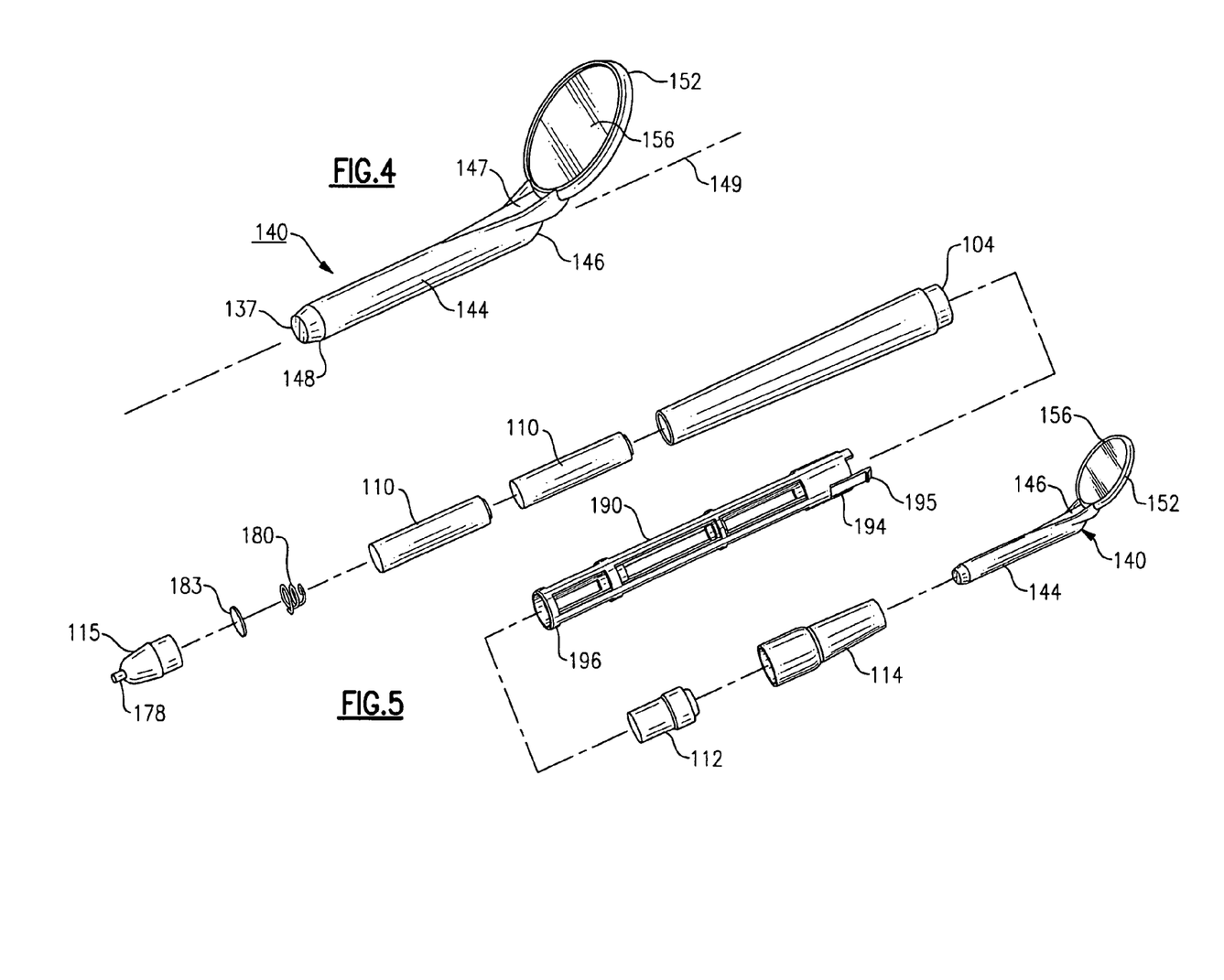
FIG. 4 is a side perspective view of the light guide of the intraoral dental examination instrument depicted in FIGS. 2 and 3.
FIG. 5 is a partial exploded view of the intraoral dental examination instrument of FIGS. 2 and 3.

Unlike the preceding described examination instrument of FIGS. 1(a) and 1(b), however, the herein described examination instrument 90 does not require an exterior power supply, the present instrument being cordless and powered by a set of stacked batteries 110 that are retained within a defined battery compartment 111, FIG. 5, that is provided in the interior of the body 108. According to this embodiment, the batteries 110 are alkaline, but can also be nickel-cadmium or other suitable type, the batteries also preferably being rechargeable.

An illumination cartridge or housing 112 is also retained according to this embodiment within the body 108 adjacent the distal end 104 thereof and distal relative to the contained batteries 110, the cartridge being described in greater detail below. The batteries 110 are retained in biased relation within the body 108 of the instrument 90 relative to the illumination cartridge 112 by means of a compression spring 180 that is positioned adjacent the rear end cap 115.

The examination instrument 100 of this specific embodiment further includes a switch assembly 170, preferably contained in the rear or proximal end of the instrument 90, the switch assembly according to this preferred embodiment including a retractable plunger 178 containing a pin that moves between respective ON and OFF positions in order to selectively provide an electrical connection between the contained batteries 110 and the illumination cartridge 112 in order to energize an LED 120 retained by the cartridge, as will be described in greater detail below.

Prior to describing the interior features of the instrument 90, and referring first to FIGS. 2-4, the mirror 140 of the herein described instrument 90 includes an elongated shank portion 144. The shank portion 144 has a proximal end 148 that includes a defined light entrance surface 137, the shank portion terminating at a heel portion 146 having a pair of opposing substantially parallel light exit surfaces 147 on each of the top and bottom sides (only the top surface is shown in FIGS. 2-4) thereof, each of which are angled relative to a primary axis 149 that extends through the shank portion. A face portion 152 is integrally formed at the distal end of the mirror 140 along an axis (not shown) coextensive with that of the heel portion 146. The face portion 152 according to this embodiment is substantially circular in configuration (though other shapes could be contemplated) and includes a non-plano mirrored surface 156. The mirror 140 according to this embodiment is entirely made from a high-quality light transmissive material, such as acrylic, polyamide, polycarbonate and the like, and is preferably molded including the face portion 152 and the mirrored surface 156. The reflective portion of the mirror assembly 140 is molded according to this embodiment using "In Mold Decoration" technology wherein the contour of the mirrored surface 156 is controlled by the shape/contour of the mold. According to this embodiment, the non-plano mirrored surface 156 is concave in curvature in order to provide magnification of the object(s) being examined. According to this embodiment, about a 1.5× magnification is created although this parameter can easily be varied. It should be noted that in the alternative that the non-plano mirrored surface 156 can also be made with a convex curvature, wherein a minified image can be produced, thereby creating a wider field of view which can be useful for certain oral applications.

Figure 6:
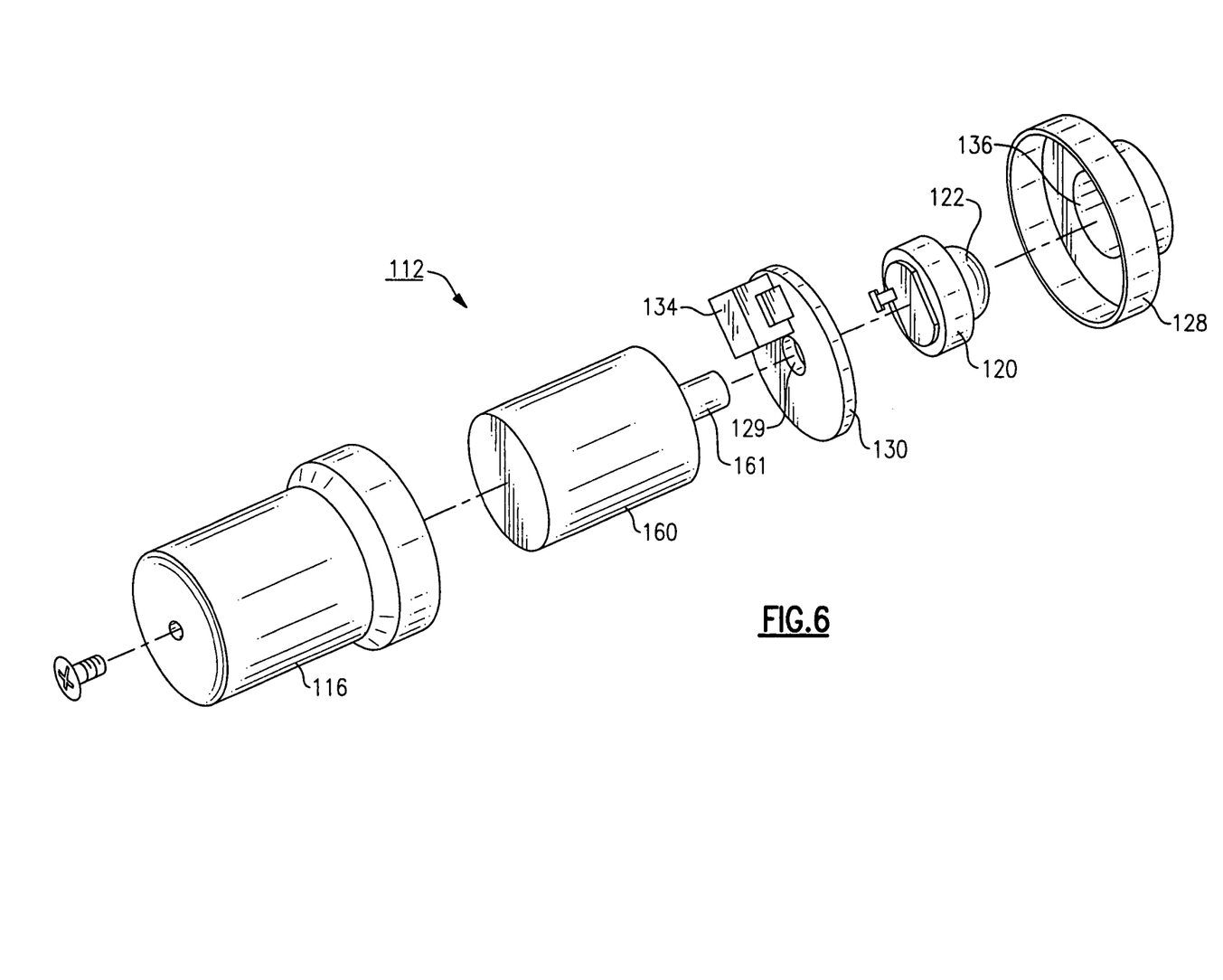
FIG. 6 is an exploded view of an illumination cartridge used in the intraoral dental examination instrument of FIGS. 2-5.
Figure 7:
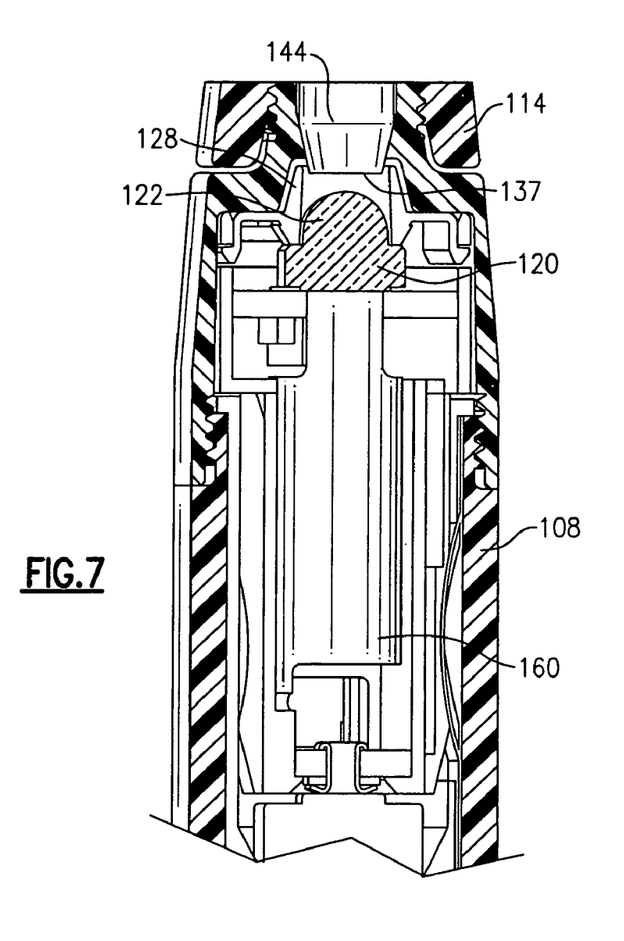
FIG. 7 is a partial sectioned view of the illumination cartridge of FIG. 6 as assembled in the intraoral dental examination instrument of FIGS. 2-5.

Referring to FIGS. 5-7, the illumination cartridge 112 of the described embodiment consists of a cylindrical housing body 116 made from Radel R, polyphenylsulfone or suitable polymer but can be fabricated from literally any electrical insulating material, wherein a miniature LED 120 is disposed at a distal end 104 adjacent a reflector cap portion 128 that is attached in overlaying relation thereto. The illumination cartridge 112 further includes a printed circuit board (PCB) 130 that contains suitable electronics 134 thereupon used for powering the miniature LED 120. The PCB 130 according to this embodiment is disposed immediately below or proximal to the miniature LED 120, and includes an opening 129 for receiving the projecting portion 161 of a heat sink 160, retained by the housing body 116 in order to dissipate heat that is generated by the miniature LED, as well as the PCB 130.

Figure 10:
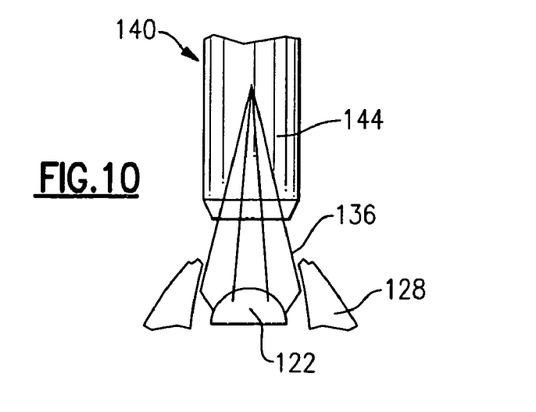
FIG. 10 is a partial diagrammatic view of the optical coupling between the illumination cartridge of FIG. 6 and the releasably attached mirror in accordance with present invention.

The reflector portion 128 is defined by a through opening 136 that is fitted about the lens envelope 122 of the miniature LED 120, the through opening preferably having an inwardly tapered surface 136 that is used in order to focus the light emitted from the miniature LED 120 onto a light entering surface 137 of the shank portion 144 of the mirror 140, as shown more particularly in FIGS. 7 and 10. The illumination cartridge 112 is retained by the front end cap 114 and is held in place by the body 108 and a contact strip 194 of an internal cage member 190. The reflector portion 128 also recesses the LED lens 122 and protects the lens from damage, such as from dropping the cartridge 114, when removed from the instrument for cleaning.

Figure 8:
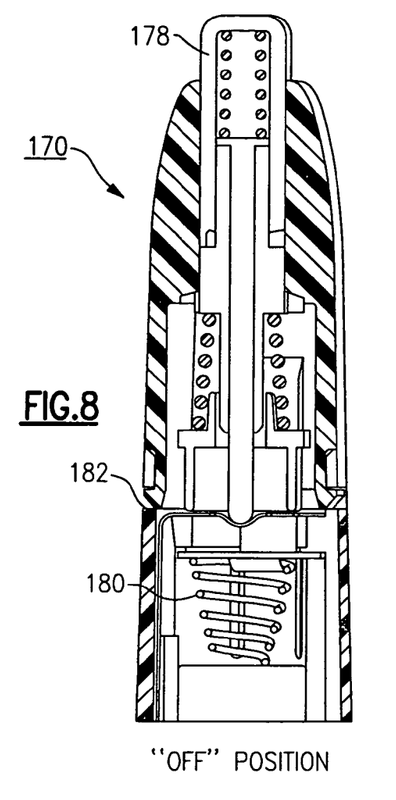
FIGS. 8 and 9 are partial side sectioned views of the dental intraoral examination instrument of FIGS. 2-4 showing a retractable switch assembly illustrating same in respective OFF and ON positions.
Figure 9:
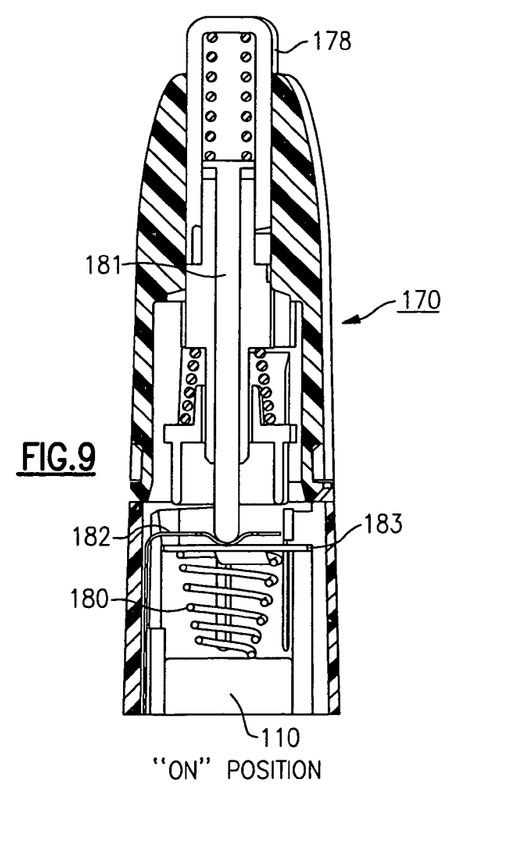

Referring to FIGS. 5, 8 and 9 and as previously noted herein, the examination instrument 90 is powered by means of a switch assembly 170 provided at the rear portion of the body 108. A retractable plunger 178 is mounted into the rear end cap 115 and includes a spring loaded pin member 181 that is selectively engageable with an S-shaped conformable spring member 182. As the retractable plunger 178 is pushed by the user from the OFF to the ON position, shown in FIGS. 8 and 9 respectively, the pin member 181 is caused to engage with the S-shaped spring member 182, which conforms and causes the battery contacts to engage with a conductive laterally extending contact strip 194 disposed on a hollow cylindrical internal cage member 190 covering the interior of the handle 108, the strip providing electrical connectivity with the contained cartridge 112, when the battery contacts engage the strip 194 as shown in FIG. 9, with the S-shaped spring member 182 in relation to electrical contacts. The internal cage 190 is used to hold and retain the conducting strip 194 and to provide centering for the batteries 110. The internal cage 190 further positions a small conductive plate 183 laterally, the plage being disposed adjacent to and proximal of the compression spring 180.

In operation, the mirror 100 is first attached to the examination instrument 90 using colleted portions (not shown) which are formed in the distal end of the handle 108. The front end cap 114 is then threaded onto the distal end of the handle 108 in order to secure the mirror 140 in place. The illumination cartridge 112 is attached to the distal end of the handle 108 by threaded portions. In this position, the shank portion 144 of the mirror 140 is situated in relation to the miniature LED 120.

The instrument 90 is initially in the "OFF" position shown in FIG. 8. As noted, depression of the retractable plunger 178 of the switch assembly 170 causes the contained pin member 181 to engage with the S-shaped spring member 182, causing relative movement of the S-shaped spring member and allowing the battery contacts to be brought into electrical contact with the illumination cartridge 112, by virtue of coextensive top and bottom ends 195, 196, respectively, of the conductive laterally extending strip 194, thereby energizing the contained LED 120. Emitted light from the miniature LED 120 is then focused, by virtue of the reflector portion 128 onto the light transmissive shank portion 144 of the mirror 100. The mirror 140 thereby provides suitable illumination at the exit surfaces 147 of the heel portion 146 and the face portion 152, wherein the non-plano mirrored surface 156 permits enhanced examination of the teeth.

Following use, the mirror 140 can be removed by reversing the threading of the front end cap 114 and pulling same from the colleted areas of the body 108. The front end cap can then be removed, permitting access to the illumination cartridge 112 can be removed by reversing the threaded portion of the body 108 and the distal cap 114 from the body 108 along with the batteries 110, once the mirror 140 has also been removed from the distal end of the examination instrument 90. Once removed, the body 108 as well as the front and rear end caps 114, 115 can then be autoclaved.

Figure 11:
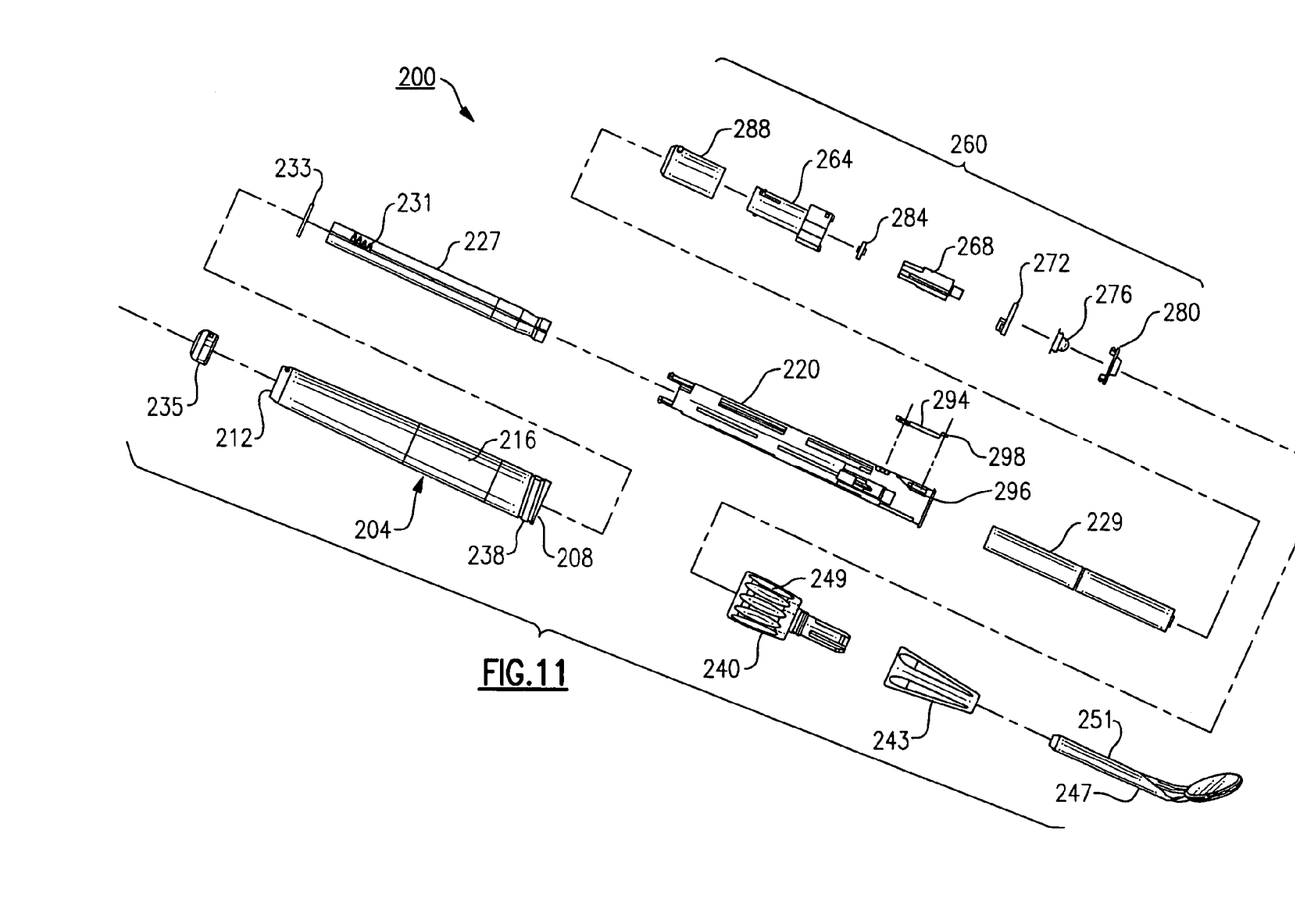
FIG. 11 is an exploded view of a dental intraoral instrument made in accordance with another preferred embodiment of the present invention.

Referring to FIG. 11, there is shown an intraoral dental examination instrument 200 made in accordance with a second preferred embodiment of the present invention. The examination instrument 200 according to this embodiment includes a plastic molded handle body 204, the body defined by a cylindrical configuration and having a pair of open ends 208, 212 that further define a hollow interior 216 which is sized for retaining a cylindrical interior cage member 220. The interior cage member 220 is preferably also made from plastic or similar insulating material which is also preferably autoclavable and includes a plurality of lateral slots that are defined along the axial length thereof, the interior cage member further having means for supporting an electrically conductive battery contact strip 227, the strip including a contact spring 231 at a proximal end thereof. The interior cage member 220 is also open-ended and has a hollow interior that defines a battery compartment which is appropriately sized for receiving a pair of stacked cadmium, alkaline or other suitable batteries 229. The contact spring 231 serves as a contact for the stacked batteries 229, relative to a battery contact disk 233 that is interposed between the contact spring and an endcap 235 that is fitted onto the proximal open end 212 of the handle body 204.

The distal end 208 of the handle body 204 of the examination instrument 200 includes a set of exterior screw threads 238 permitting the connection of a mirror support collet 240, as well as a collet locking ring 243 that retains a disposable mirror 247. The mirror support collet 240 is defined by a rotatable exterior knob 249 that includes a set of interior threads (not shown). The collet locking ring 243 is threadingly mounted onto the exterior of the mirror support collet 240, while the disposable mirror 247 includes an elongate shank portion 251 that is engaged with the collet locking ring, the collet locking ring being rotated to tighten or loosen the grip on the disposable mirror to permit engagement or disengagement therewith. The mirror 247 is similar in design to that previously described having the shank portion 251, a face portion and further including a non-plano reflective surface.

Disposed between the stacked batteries 229 and the mirror support collet 240 is an illumination assembly 260 that includes a hollow cylindrical cartridge body 264 containing a plurality of interconnected components. Among these contained components are a heat sink 268 onto which is packaged an LED driver circuit board 272. A miniature LED package 276 is disposed distally from the LED package 276 as well as a cartridge cap 280 having an inwardly tapered surface that is used to focus light from the miniature LED onto a light entering surface of the disposable mirror 247. A battery contact board 284 is disposed in the bottom of the cartridge body 264, each of which are held by a cartridge collar 288 that accommodates the illumination cartridge assembly 260 within the distal end of the handle body 204, when assembled thereto.

The herein described dental examination instrument 200 further utilizes a rotary switch assembly in order to selectively illuminate the miniature LED package 276 that is housed in the illumination cartridge assembly 260. The rotary switch assembly is enabled by rotating the rotatable exterior knob 249 of the mirror support collet 240 relative to the threads 238 of the distal end of the body 204 causing the illumination cartridge 260 to move into contact with the batteries 229. Creating a negative electrical contact as the batteries 229 are pushed axially against spring 231, with the strip 227 and contact disk 233, the strip 227 contacts cartridge collar 288. The battery contact board 284 contacts the positive battery terminals completing the circuit and energizing the LED 276.

Figure 12:
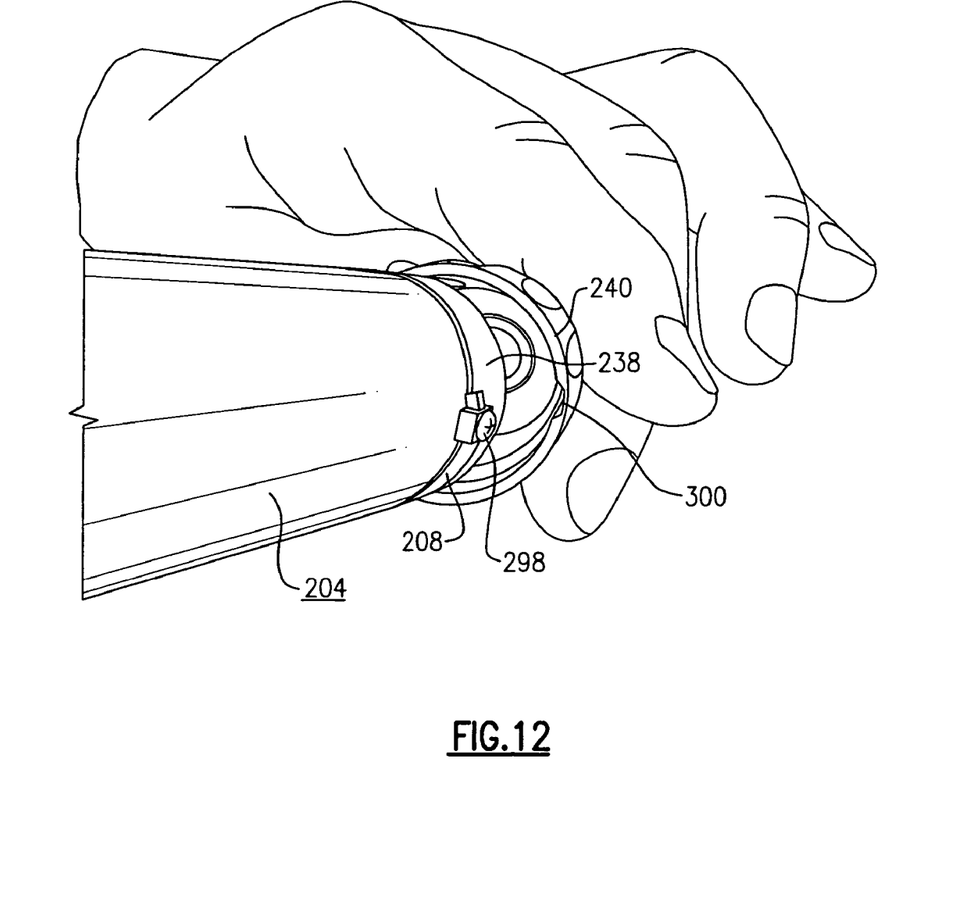
FIG. 12 is an enlarged perspective view of a portion of the instrument of FIG. 11 depicting a mechanical detent used therewith.

Referring to FIGS. 11 and 12 and in order for the user to properly sense actuation of the LED 276, a spring member 294 is preferably sandwiched between the exterior of the internal cage member 220 and the interior of the body 204. The spring member 294, in this instance, a leaf spring, is fastened at one end to a slot of the internal cage member adjacent the distal end thereof 220 by conventional means, in this case, by means of an interference fit, the spring member including a depending engagement end portion 298 that initially resides in a groove 296 which is provided at the distal end of the internal cage member 220. When the internal cage member is inserted into the interior of the body 208, the spring member 294 is biased such that the engagement end portion 298 is caused to extend through a small opening (not shown) that is provided in the external threads 238 of the body 204 that is sized to accommodate same.

In operation, the mirror support collet 240 is attached to the distal end of the body 204 by threading the internal threaded portion thereof with the external threads 238 provided on the distal end 208 of the body. As the collet supporting ring 243 and collet 240 are rotated thereupon in a clockwise manner to initiate engagement, the LED 276 is caused to illuminate due to the above electrical connection that is created between the illumination cartridge 260, including the contained LED, and the batteries 229. As the above procedure is reversed, the LED 276 is deenergized upon counterclockwise rotation of the collet supporting ring 243 and collet 240 relative to the body 204 of the instrument whereupon the engagement end portion 298 is arranged relative to a hollow depression that is formed on the interior of the collet 240 into which the engagement end portion repeatably slips when the LED OFF position is reached as mechanically sensed by the user in the form of a detent.

| PARTS LIST FOR FIGS. 1-12 | |
|---|---|
| 20 | dental intraoral examination instrument |
| 24 | elongated body portion |
| 25 | gripping handle |
| 26 | slotted vent holes |
| 28 | front end cap |
| 32 | back end cap |
| 36 | distal end |
| 40 | mirror |
| 40a | shank portion |
| 40b | heel portion |
| 40c | face portion |
| 48 | electrical cord |
| 52 | wires |
| 56 | cord grip |
| 61 | opening |
| 62 | lamp assembly unit |
| 66 | electrical connectors |
| 70 | lamp |
| 74 | heat sink |
| 78 | lens |
| 90 | dental intraoral examination instrument |
| 100 | mirror |
| 104 | distal end |
| 108 | body |

-continued

PARTS LIST FOR FIGS. 1-12

| | |
|---|---|
| 110 | batteries |
| 112 | illumination cartridge |
| 114 | front end cap |
| 115 | rear end cap |
| 116 | housing body |
| 120 | LED |
| 122 | lens envelope |
| 124 | distal end |
| 128 | reflector portion |
| 130 | printed circuit board |
| 131 | opening |
| 132 | through opening |
| 134 | electrodes |
| 136 | inwardly tapered surface |
| 137 | light entering surface |
| 140 | mirror |
| 144 | shank portion |
| 146 | heel portion |
| 147 | light exit surface |
| 148 | proximal end |
| 149 | primary axis |
| 152 | face portion |
| 156 | non-piano mirrored surface |
| 170 | retractable switch assembly |
| 178 | plunger |
| 180 | spring, compression |
| 181 | pin member |
| 182 | spring member, etc. |
| 183 | conductive plate |
| 190 | internal case member |
| 194 | laterally extending electrical contact strip |
| 195 | top end, strip |
| 196 | bottom end, strip |
| 200 | intraoral dental examination instrument |
| 204 | handle body |
| 208 | open end |
| 212 | open end |
| 216 | hollow interior |
| 220 | interior cage member |
| 227 | electrically conductive battery contact strip |
| 229 | batteries |
| 231 | contact spring |
| 233 | battery contact disk |
| 235 | endcap |
| 240 | mirror support collet |
| 243 | collet supporting ring |
| 247 | disposable mirror |
| 251 | elongate portion |
| 260 | illumination cartridge assembly |
| 264 | cartridge body |
| 268 | heat sink |
| 272 | LED driver circuit board |
| 276 | LED package |
| 280 | cartridge cap |
| 284 | battery contact board |
| 288 | cartridge collar |
| 290 | rotary switch assembly |
| 294 | spring member |
| 296 | groove |
| 298 | engagement end portion |
| 300 | hollow depression |

Other variations and modifications will be readily apparent to one of sufficient skill in the field that embody the inventive concepts taught in the above specification and are recited in the following claims.

We claim:

1. An illumination assembly for an intraoral dental examination instrument, said illumination assembly comprising:
    a compact housing having an interior that retains at least one LED;
    a heat sick disposed in the interior of said housing;
    an electrical contact at a proximal end of said housing, to enable electrical coupling of said at least one retained LED with a power supply of said examination instrument;
    at least one circuit board disposed in said interior of said housing in relation to said at least one retained LED; and
    a protective reflector cap attached to a distal end of said housing, said reflector cap having a through opening and further including an interior surface that surrounds a lens envelope of said at least one LED so as to focus light from said at least one LED onto an attached transmissive mirror and protects said at least one LED from damage, said interior surface tapering inwardly from a first diameter adjacent said at least one LED to a second diameter at said through opening, said second diameter being smaller than said first diameter, said illumination assembly being entirely contained within said compact housing, wherein said housing is solely and selectively insertable into and removable from the interior of said examination instrument without having to remove any other components from the interior of said instrument,
    wherein said at least one circuit board includes an opening for receiving a projecting portion of said heat sink.

2. An illumination assembly as recited in claim 1, wherein said inwardly tapered interior surface of said reflector cap permits light rays from said at least one retained LED to be substantially focused onto a light guide.

3. An illumination assembly as recited in claim 1, wherein said power comprises at least one battery contained within said instrument.

4. An intraoral dental examination instrument comprising:
    an elongated handle;
    a mirror disposed in relation to a distal end of said elongated handle; and entrance surface of said mirror, said illumination assembly including a housing having an interior sized to retain at least one LED, a heat sink, and at least one circuit board disposed in relation to said heat sink, said illumination assembly further including a reflector cap attached to a distal end of said housing, said reflector cap having a through opening and further including an inwardly tapered interior surface, said inwardly tapered interior surface surrounding a LED lens envelope to permit illumination from said at least one LED to be focused onto said light entrance surface of said mirror and for covering and protecting said at least one LED to protect said at least one LED from damage if said housing is dropped, wherein said illumination assembly, that is entirely contained within said housing, is solely and releasably removable from an insertable within said handle, said housing being removable without having to remove any other components from said handle to permit easy insertion and removal therefrom.

5. An instrument as recited in claim 4, including a self-contained power supply disposed within said handle and means for electrically coupling said power supply to said at least one retained LED within said housing.

6. An instrument as recited in claim 5, wherein said mirror is releasably attachable to said handle.

7. An instrument as recited in claim 4, wherein said handle is autoclavable.

8. An instrument as recited in claim 7, wherein said at least one circuit board includes an opening sized for receiving a projection portion of said heat sink.

9. An instrument as recited in claim 4, wherein said handle is autoclavable.

10. An instrument as recited in claim 4, wherein said electrically coupling means includes a switch assembly for selectively energizing said at least one LED.

11. An instrument as recited in claim 10, wherein said switch assembly includes a retractable plunger movable between a first and a second position for selectively creating electrical contact between the at least one contained battery and said at least one retained LED.

12. An instrument as recited in claim 11, including means for biasing said retractable plunger in each of said first and second positions.

13. An instrument as recited in claim 10, wherein said switch assembly is enabled by rotation of a front end cap of said instrument relative to said handle, said at least one battery and said illumination assembly being caused to move unitarily in relation to a spring biased contact when said front end cap is rotated.

14. An instrument as recited in claim 13, including a detent mechanism for detecting by a user when said switch assembly has been enabled to one of an OFF position and an ON position.

15. A cordless intraoral dental examination instrument comprising:
   an elongated handle;
   at least one battery for powering said instrument, said at least one battery being contained in said handle;
   a mirror disposed in relation to a distal end of said handle; and
   an illumination cartridge disposed in said handle proximate a light entrance surface of said mirror, said illumination cartridge including a housing sized to retain at least one LED, at least one circuit board connected to said at least one LED, and means for selectively energizing said at least one LED wherein said of said at least one battery and said illumination cartridge are centered and retained within an internal sleeve member disposed within said elongated handle, said interval sleeve member including a plurality of longitudinal slots, at least one said slots being sized to retain a conductive strip member having one end in contact with said illumination cartridge and an opposite end disposed in relation in relation to said at least one battery.

16. An instrument as recited in claim 15, wherein said selective interconnecting means includes a switch assembly, said switch assembly including a movable component that permits engagement of said conductive strip member with said battery for energizing said at least one LED.

17. An instrument as recited in claim 16, wherein said switch assembly includes a retractable plunger movable between a first position and a second position.

18. An instrument as recited in claim 17, wherein said retratable plunger is disposed at a proximal end of said handle.

19. An instrument as recited in claim 16, wherein said movable component is a front end cap that is rotatably connected to said handle to cause movement of said cartridge and said at least one battery unitarily against a spring-biased contact wherein engagement of said battery with said spring-biased contact completes electrical contact with said conductive strip member.

20. An instrument as recited in claim 17, including a detent mechanism for indicating to a user when said LED is one of an OFF position and an ON position.

21. An instrument as recited in claim 15, wherein said illumination cartridge is releasably removable from said handle.

22. An instrument as recited in claim 21, wherein said illumination cartridge includes a reflector cap portion disposed at a distal end thereof, said reflector cap portion including a through opening and a inwardly tapering interior surface that surrounds the lens envelope of said at least one LED so as to substantially focus the light rays emitted by said at least one LED and protect the at least one LED from damage when said cartridge is removed from said instrument.

* * * * *